United States Patent
Reydel et al.

(10) Patent No.: US 7,736,372 B2
(45) Date of Patent: Jun. 15, 2010

(54) APPARATUS AND METHODS FOR ENDOSCOPIC SUTURING

(75) Inventors: Boris Reydel, West Caldwell, NJ (US); Cang Lam, Irvine, CA (US); Richard C. Ewers, Fullerton, CA (US); Rodney Brenneman, San Juan Capistrano, CA (US); Vahid Saadat, Saratoga, CA (US)

(73) Assignee: USGI Medical, Inc., San Clemente, CA (US)

( * ) Notice: Subject to any disclaimer, the term of this patent is extended or adjusted under 35 U.S.C. 154(b) by 447 days.

(21) Appl. No.: 10/986,461

(22) Filed: Nov. 10, 2004

(65) Prior Publication Data

US 2005/0119671 A1     Jun. 2, 2005

Related U.S. Application Data

(60) Provisional application No. 60/519,881, filed on Nov. 13, 2003.

(51) Int. Cl.
  *A61B 17/04*   (2006.01)
(52) U.S. Cl. ........................ 606/148; 606/139; 606/205
(58) Field of Classification Search ......... 606/139–149, 606/167, 170, 205, 206, 151, 153, 157, 108; 600/101–183, 201–211
  See application file for complete search history.

(56) References Cited

U.S. PATENT DOCUMENTS 4,006,747 A * 2/1977 Kronenthal et al. ......... 606/144
4,235,238 A * 11/1980 Ogiu et al. .................. 606/145
5,037,433 A   8/1991 Wilk et al.
5,480,405 A * 1/1996 Yoon .......................... 606/139

(Continued)

FOREIGN PATENT DOCUMENTS

WO   WO 02/060328 A1   8/2002

(Continued)

OTHER PUBLICATIONS

Chuttani et al., "A Novel Endoscopic Full-Thickness Plicator for Treatment of GERD: An Animal Model Study," *Gastrointestinal Endoscopy*, vol. 26, No. 1, (2002), pp. 116-122.

(Continued)

*Primary Examiner*—Anhtuan T Nguyen
*Assistant Examiner*—Kathleen Sonnett
(74) *Attorney, Agent, or Firm*—Levine Bagade Han LLP; Charles C. Fowler (57) ABSTRACT

Apparatus & methods for endoscopic suturing are described herein. A distal tip of the endoscopic device engages the tissue and then approximates the engaged tissue to form a tissue fold. A needle body positioned within a flexible catheter is deployed into or through the newly created tissue fold where it is then detached or released from the endoscopic device. The needle body has a length of suture which depends therefrom and can be used to secure the tissue fold. The entire endoscopic device or its tissue engaging assembly can then be rotated relative to the tissue fold while maintaining engagement with the tissue to maneuver the flexible catheter to the opposing side of the penetrated tissue fold. This procedure can be repeated any number of times to create an interrupted, continuous, or running suture to secure the tissue fold.

9 Claims, 9 Drawing Sheets

U.S. PATENT DOCUMENTS

| | | | | |
|---|---|---|---|---|
| 5,643,294 | A | * | 7/1997 | Tovey et al. ................. 606/148 |
| 5,810,876 | A | * | 9/1998 | Kelleher ..................... 606/205 |
| 5,865,724 | A | * | 2/1999 | Palmer et al. ............... 600/104 |
| 5,954,731 | A | | 9/1999 | Yoon |
| 5,954,733 | A | * | 9/1999 | Yoon .......................... 606/147 |
| 5,993,466 | A | * | 11/1999 | Yoon .......................... 606/147 |
| 6,017,358 | A | | 1/2000 | Yoon et al. |
| 6,086,601 | A | * | 7/2000 | Yoon .......................... 606/148 |
| 6,352,503 | B1 | * | 3/2002 | Matsui et al. ............... 600/104 |
| 6,383,199 | B2 | * | 5/2002 | Carter et al. ................ 606/148 |
| 6,503,264 | B1 | * | 1/2003 | Birk ........................... 606/191 |
| 6,648,816 | B2 | * | 11/2003 | Irion et al. .................. 600/173 |
| 6,821,285 | B2 | * | 11/2004 | Laufer et al. ............... 606/153 |
| 6,835,199 | B2 | | 12/2004 | McGuckin, Jr. et al. |
| 6,921,361 | B2 | * | 7/2005 | Suzuki et al. ............... 600/106 |
| 7,261,728 | B2 | * | 8/2007 | Long et al. .................. 606/207 |
| 2002/0111534 | A1 | * | 8/2002 | Suzuki et al. ............... 600/102 |
| 2003/0176890 | A1 | | 9/2003 | Buckman et al. |
| 2004/0111019 | A1 | * | 6/2004 | Long .......................... 600/407 |
| 2004/0138529 | A1 | * | 7/2004 | Wiltshire et al. ............ 600/144 |
| 2004/0193117 | A1 | | 9/2004 | Laufer et al. |
| 2004/0193184 | A1 | | 9/2004 | Laufer et al. |
| 2004/0193193 | A1 | | 9/2004 | Laufer et al. |
| 2004/0193194 | A1 | | 9/2004 | Laufer et al. |
| 2004/0194790 | A1 | | 10/2004 | Laufer et al. |
| 2004/0215216 | A1 | | 10/2004 | Gannoe et al. |
| 2004/0243152 | A1 | | 12/2004 | Taylor et al. |
| 2004/0249362 | A1 | | 12/2004 | Levine et al. |
| 2004/0249392 | A1 | | 12/2004 | Mikkaichi et al. |
| 2004/0249395 | A1 | | 12/2004 | Mikkaichi et al. |
| 2005/0033320 | A1 | | 2/2005 | McGuckin, Jr. et al. |
| 2005/0033328 | A1 | | 2/2005 | Laufer et al. |
| 2005/0043758 | A1 | * | 2/2005 | Golden et al. ............... 606/206 |
| 2005/0049617 | A1 | | 3/2005 | Chatlynne et al. |

FOREIGN PATENT DOCUMENTS

| | | |
|---|---|---|
| WO | WO 03/092509 A1 | 11/2003 |
| WO | WO 03/094785 A1 | 11/2003 |
| WO | WO 03/105732 A1 | 12/2003 |
| WO | WO 2004/004542 A2 | 1/2004 |
| WO | WO 2004/019788 A2 | 3/2004 |
| WO | WO 2004/021894 A1 | 3/2004 |
| WO | WO 2004/103189 A1 | 12/2004 |
| WO | WO 2005/004727 A1 | 1/2005 |

OTHER PUBLICATIONS

Mason, "Development of Future of Gastroplasties for Morbid Obesity," *Arch Surg*, vol. 138 (Apr. 2003), pp. 362-366.

\* cited by examiner

APPARATUS AND METHODS FOR ENDOSCOPIC SUTURING

CROSS-REFERENCES TO RELATED APPLICATIONS

This application claims the benefits of priority to U.S. Provisional Pat. App. Ser. No. 60/519,881 filed Nov. 13, 2003, which is incorporated herein by reference in its entirety.

BACKGROUND OF THE INVENTION

Field of the Invention

The present invention relates to apparatus and methods for endoscopically forming and suturing tissue. More particularly, the present invention relates to apparatus and methods for endoscopically forming tissue folds and continuously suturing those folds.

Various devices and methods for grasping free ends or lengths of suture and passing the suture material through tissue are known. One method generally involves attaching a suture end to a needle and passing the needle through the tissue using a needle manipulating device. Once passed through the tissue, another device is typically employed to retrieve or otherwise manipulate the needle and suture.

Other methods generally utilize sharpened needle tips which are configured to retain a suture. The needle tip is then able to penetrate the tissue and leave the suture end on the far side of the tissue where it can be grasped for further manipulation. Such grasping mechanisms generally employ various configurations such as the use of wire-like hooking elements, looped wires, etc. Some devices employ suture grasping elements, such as forceps jaws, with sharpened tips to grasp and pass the suture material.

However, many of the conventional devices have limitations in applications such as closed surgery, especially arthroscopic or laparoscopic surgery, where space and visibility constraints at the surgical site render it difficult to fully extend a suture grasping device to easily grasp a suture. Moreover, many of the devices are constrained to regions within the body accessible via straight-line access. This is typically due to the rigidity of the tool shaft upon which the graspers or needles are employed.

Furthermore, because of the typical size and rigidity of the tool, such a suture passing instrument is typically inserted within a patient as a separate tool which occupies valuable space. Additionally, other tools are typically needed to facilitate the manipulation of the suture material through the tissue.

BRIEF SUMMARY OF THE INVENTION

In forming or securing folds of tissue, e.g., in the gastrointestinal (GI) tract such as the stomach of a patient, tissue folds may be formed to treat various conditions such as obesity. Such treatments may be effected via an endoscopic device designed to engage a tissue wall, create one or more tissue folds, and secure the tissue fold(s) with tissue anchors and/or suture.

One such endoscopic device described herein may have a primary grasper at a distal tip of the endoscopic device configured to engage the tissue and then approximate the engaged tissue to a proximal position relative to the catheter tip, thereby providing a uniform plication of predetermined size. A needle body detachably or removably positioned within a flexible catheter or launch tube may be deployed from the launch tube such that it passes at least partially within or entirely through the fold formed by the approximated tissue. The needle body may also have a length of suture attached thereto for passage through the tissue fold. Once the needle body has been penetrated into or through the tissue fold, it may be detached or released from the endoscopic device via a secondary needle grasper. A description of one or more endoscopic devices which may be utilized to initially form the one or more tissue folds may be seen in further detail in U.S. patent application Ser. No. 10/735,030 filed Dec. 12, 2003, which is incorporated herein by reference in its entirety.

The needle body itself may generally be configured as a needle having one or two tapered piercing ends on opposing sides of the needle body. A suture attachment point, e.g., an eyelet or opening, may be defined along the needle body and serve as an attachment point for a length of suture. Alternatively, an expandable anchor may also be positioned within a needle body for passage through tissue. Once free of the tissue, the anchor may be deployed from the needle body for placement against the tissue. Other variations of the needle body and grasper may be seen in further detail in U.S. patent application Ser. No. 10/989,684 filed Jul. 23, 2004, which is incorporated herein by reference in its entirety.

In operation, once the needle body has been advanced through or at least partially through the tissue fold, the needle body may be released by the secondary needle grasper and the entire endoscopic device or its tissue engaging assembly may then be rotated relative to the opposite side of the tissue fold, i.e., on the side of the tissue where the needle body exits the tissue fold, while maintaining engagement with the tissue via the primary grasper to maneuver the catheter or launch tube to the opposing side of the penetrated tissue fold. The rotatable primary grasper may keep its grasp on the tissue fold to maintain a position of the device relative to the tissue fold and needle body. The length of suture remains attached to the needle body and is routed through the tissue passage created by the needle body.

The secondary grasper may then be used to grasp onto the needle body and while holding the needle body, the entire apparatus may again be rotated to realign the needle launch tube back to the other side of the tissue fold. Once the needle body has been desirably positioned, it may again be manipulated to align the catheter distal tip transversely relative to the tissue fold which may again be pierced by advancing the needle body into or through the tissue fold at another location adjacent to the originally formed tissue passage. This process may be repeated any number of times to form a continuous or running suture depending upon the desired length of suture and the desired suturing effects.

Additionally, a gastroscope having a sufficiently small-sized diameter may be introduced into the area by advancing the gastroscope through a lumen defined through the endoscopic device to provide endoscopic visualization of the procedure. Alternatively, a gastroscope may be may be attached or connected to a tubular member disposed externally of the endoscopic device. In another alternative, an imager may be directly integrated into the distal tip of the endoscopic device.

DETAILED DESCRIPTION OF THE INVENTION

Various methods and devices for forming and/or securing folds of tissue, e.g., in the gastrointestinal (GI) tract such as the stomach of a patient, are presented herein. Such tissue folds may be formed to treat various conditions, for example, for the treatment of obesity by approximating the walls of a gastrointestinal lumen to narrow the lumen and thereby reduce the area for absorption in the stomach or intestines. Such treatments may be effected via an endoscopic device that engages a tissue wall of the gastrointestinal lumen, creates one or more tissue folds, and secures the tissue fold(s) with tissue anchors and/or suture. The suture is preferably disposed through the muscularis and/or serosa layers of the gastrointestinal tissue, as described in further detail below.

In operation, a distal tip of the endoscopic device engages the tissue and then approximates the engaged tissue to a proximal position relative to the catheter tip, thereby providing a uniform plication of predetermined size. A needle body detachably or removably positioned within a flexible catheter or launch tube may be deployed from the launch tube such that it passes at least partially within or entirely through the fold formed by the approximated tissue. The needle body may also have a length of suture attached thereto for passage through the tissue fold.

Once the needle body has been penetrated into or through the tissue fold, it may be detached or released from the endoscopic device. The entire endoscopic device or its tissue engaging assembly may then be rotated relative to the tissue fold while maintaining engagement with the tissue to maneuver the catheter or launch tube to the opposing side of the penetrated tissue fold.

Formation of a tissue fold may be accomplished using at least two tissue contact areas that are separated by a linear or curvilinear distance, wherein the separation distance between the tissue contact points affects the length and/or depth of the fold. In operation, a tissue grasping assembly engages or grasps the tissue wall in its normal state (i.e., non-folded and substantially flat), thus providing a first tissue contact area. The first tissue contact area then is moved to a position proximal of a second tissue contact area to form the tissue fold. The tissue anchor assembly then may be extended across the tissue fold at the second tissue contact area. Optionally, a third tissue contact point may be established such that, upon formation of the tissue fold, the second and third tissue contact areas are disposed on opposing sides of the tissue fold, thereby providing backside stabilization during extension of the anchor assembly across the tissue fold from the second tissue contact area.

Preferably, the first tissue contact point is used to engage and then stretch or rotate the tissue wall over the second tissue contact point to form the tissue fold. The tissue fold may then be approximated to a position wherein a portion of the tissue fold overlies the second tissue contact point at an orientation that is normal to the tissue fold. A needle body and suture may then be delivered across the tissue fold at or near the second tissue contact point. A description of one or more endoscopic devices which may be utilized to initially form the one or more tissue folds may be seen in further detail in U.S. patent application Ser. No. 10/735,030 filed Dec. 12, 2003, which is incorporated herein by reference in its entirety.

Figure 1A:
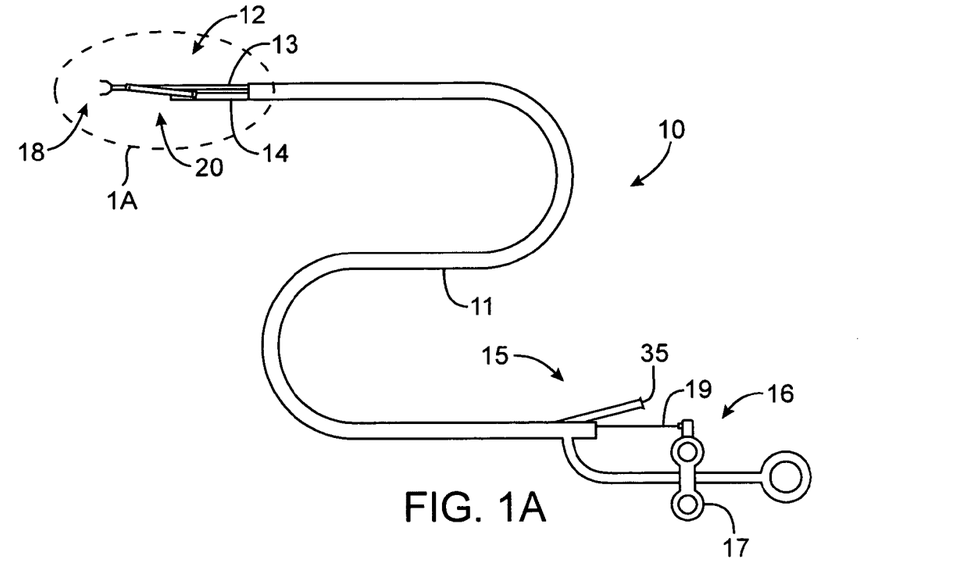
FIGS. 1A and 1B show a side view and detail view, respectively, of one variation of an endoscopic device for forming and suturing a tissue fold within a hollow body organ.

Referring to FIG. 1A, apparatus 10 generally comprises torqueable catheter or tubular member 11 having distal region 12 from which a first and a second flexible tube 13, 14, respectively, may extend. First and second tubes 13, 14 may be interconnected to one another along their lengths and are preferably interconnected near their distal ends in a pivoting manner, as described below. Proximal region 15 of apparatus 10 may be operably connected to handle 16 and actuator 17, which may actuate the distal region 12 of apparatus 10. Catheter or tubular member 11 may generally be configured for insertion through a patient's mouth and esophagus into the gastrointestinal lumen. Tissue grabbing assembly 18 is disposed on the distal end of flexible tube 13, and is operably coupled to actuator 17 via one or more control wires 19 that extend through flexible tube 13. Tissue grabbing assembly 18 is shown illustratively as a grasper but may be configured in a variety of other alternative tissue grasping assemblies.

Figure 1B:
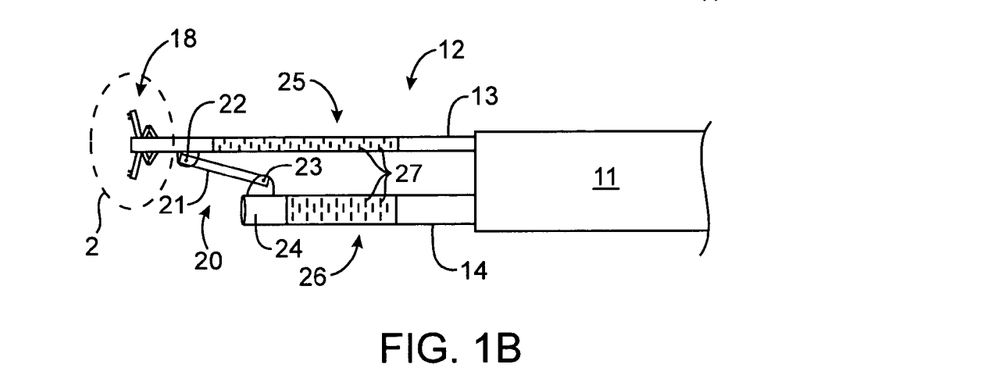

As better illustrated in FIG. 1B, flexible tubes 13 and 14 may be connected via hinge assembly 20 that comprises link 21 attached to flexible tube 13 at pivot point 22 and attached to flexible tube 14 at pivot point 23. Hinge assembly 20 may be configured to prevent tissue grabbing assembly 18 from moving more than a predetermined distance relative to distal end 24 of flexible tube 14.

Flexible tubes 13 and 14 preferably include bendable sections 25 and 26, respectively. The bendable sections 25 and 26 may comprise, for example, a plurality of through-wall slots 27 to enhance flexibility of the tube. Preferably, flexible tubes 13 and 14 are made from polymeric materials or biocompatible metals such as Nitinol or stainless steel with an etched or laser-cut slot pattern. The through-wall slots 27 may be configured as a sinusoidal repeating pattern of slots perpendicularly defined relative to the longitudinal axis of tubes 13 and 14. Alternative flexible patterns will be apparent to those of skill in the art.

Figure 2A:
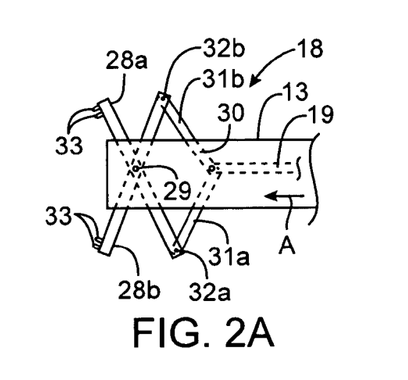
FIGS. 2A and 2B show side-sectional views of a tissue grasping assembly suitable for use with the endoscopic device of FIGS. 1A and 1B.
Figure 2B:
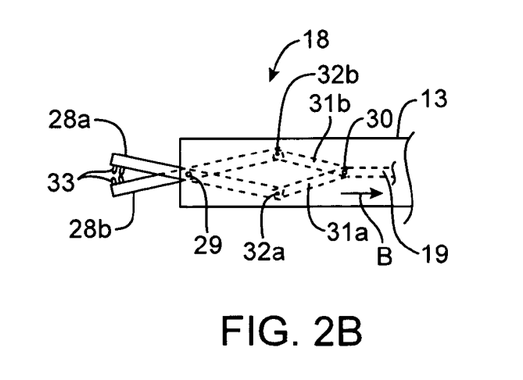

Referring to FIGS. 2A and 2B, tissue grabbing assembly 18 may comprises a pair of jaws 28a, 28b arranged to rotate about pivot point 29 between an open configuration (FIG. 2A) and a closed configuration (FIG. 2B). One or more control wires, shown here as a single control wire 19, is coupled via pivot point 30 to arms 31a and 31b. Arms 31a and 31b are in turn pivotally coupled to jaws 28a and 28b, respectively, at pivot points 32a and 32b. Each of jaws 28a and 28b may include sharpened teeth 33 or protrusions disposed near its distal ends to facilitate grasping of the tissue wall of the GI lumen.

Control wire 19 is coupled to actuator 17 of handle 16 so that translation of the wire 19 within flexible tube 13 causes the jaws 28a, 28b to open or close. In particular, urging control wire 19 distally (as indicated by arrow A in FIG. 2A) moves pivot point 30 distally, thereby forcing the jaws 28a, 28b to open. Urging control wire 19 proximally (as indicated by arrow B in FIG. 2B) moves pivot point 30 proximally, thereby forcing the jaws 28a, 28b to close together. In alternative variations, tissue grabbing assembly 18 may comprise, e.g., a corkscrew, suction ports, grappling hook or fork, a plurality of needles coupled to the distal end of flexible tube 13, etc.

Flexible tube 14 may be affixed to and immovable within catheter 11, while flexible tube 13 is coupled to catheter 11 via hinge 20. Accordingly, when control wire 19 is extended in the distal direction, flexible tube 13 is carried in the distal direction. When control wire 19 is retracted in the proximal direction, flexible tube remains stationary until jaws 28a and 28b close together, after which further retraction of control wire 19 by moving actuator 17 causes flexible tube 13 to buckle in bendable region 25, as described below.

Figure 3A:
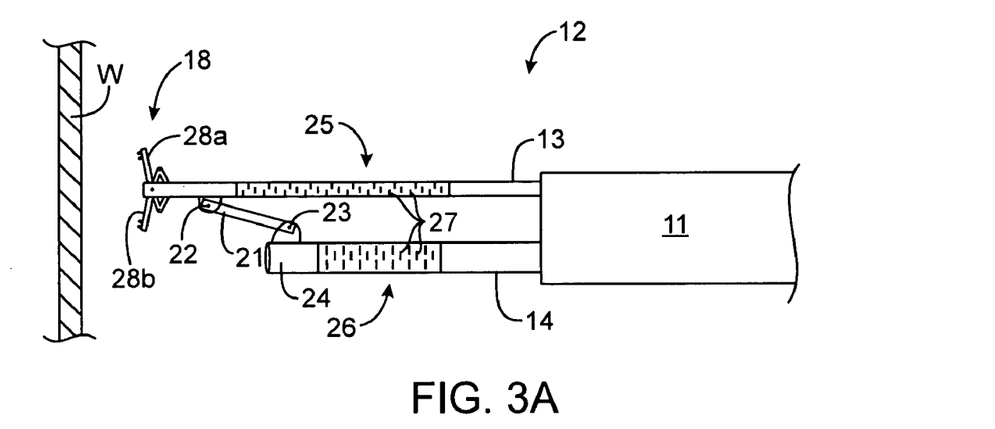
FIGS. 3A to 3E show side views illustrating one example of a method for forming a tissue fold with the device of FIGS. 1A and 1B.
Figure 3B:
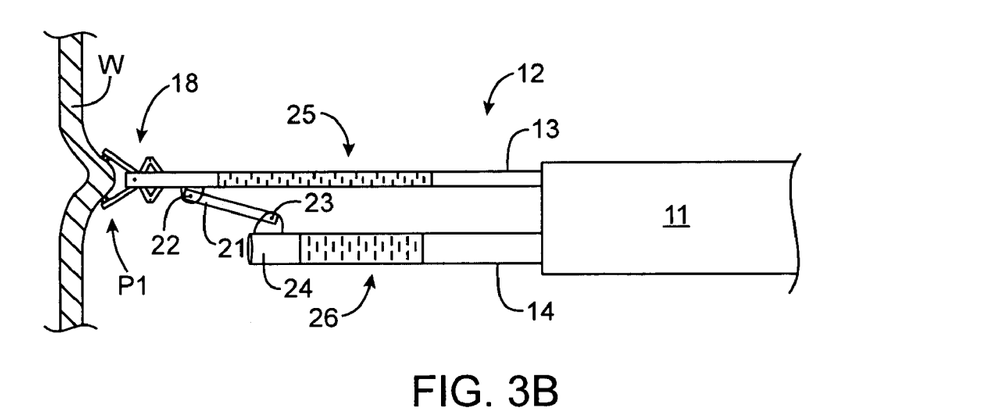

Referring now to FIGS. 1 and 3A-3E, operation of apparatus 10 is described for creating a tissue fold in a tissue wall of a GI lumen. In FIG. 3A, distal region 12 of catheter 11 is positioned within a patient's GI lumen transesophageally, and jaws 28a and 28b of tissue grabbing assembly 18 are opened by moving actuator 17 to the distal-most position on handle 16. As depicted in FIG. 3B, actuator 17 may then be moved proximally until the jaws of tissue grabbing assembly 18 engage a portion of tissue wall W at contact point P1.

Figure 3C:
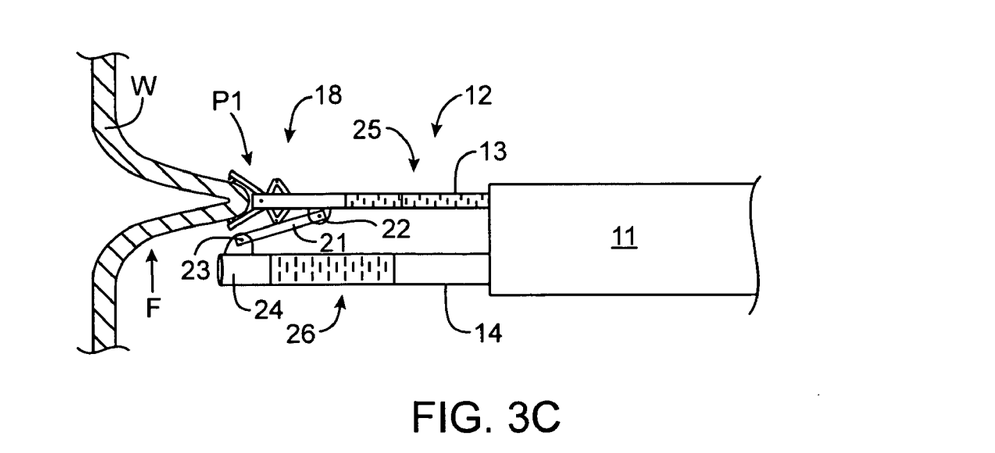

Referring to FIG. 3C, after the tissue wall W has been engaged at contact point P1, flexible tube 13 is urged proximally within catheter 11 by further proximal retraction of control wire 19 to stretch tissue wall W and create tissue fold F. During this movement of flexible tube 13, link 21 of hinge assembly 20 causes tissue grabbing assembly 18 to move from a position distal to distal end 24 of flexible tube 14, to a position proximal of distal end 24 of flexible tube 14. Bendable sections 25 and 26 of flexible tubes 13 and 14, respectively, may accommodate any lateral motion caused by operation of hinge assembly 20. Advantageously, formation of fold F facilitates the penetration of the tissue wall W by a needle and subsequent delivery of an anchor assembly or passage of a length of suture, as described hereinafter.

Figure 3D:
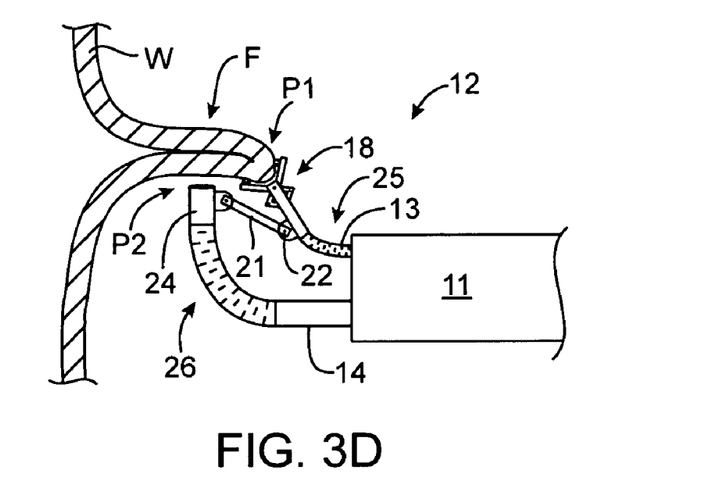
Figure 3E:
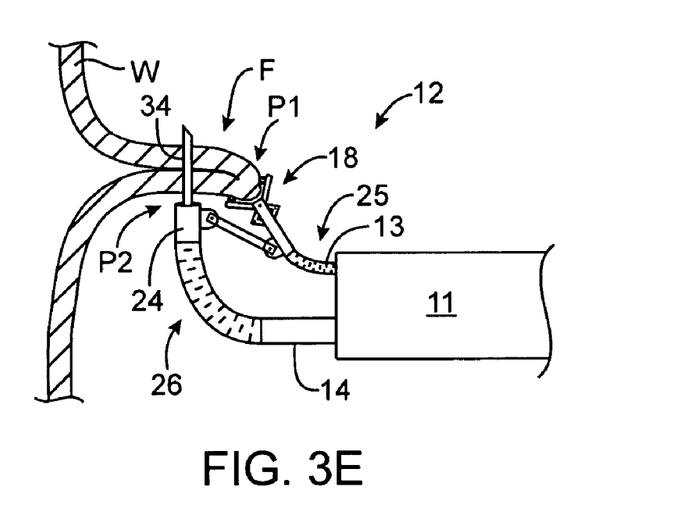

Referring to FIG. 3D, additional proximal movement of actuator 17 causes flexible tubes 13 and 14 to buckle at bendable sections 25 and 26. Hinge assembly 20 transmits force applied to flexible tube 13 via control wire 19 and actuator 17 to the distal tip 24. Preferably, flexible tube 14 is configured so that distal tip 24 contacts, and is generally perpendicular to tissue fold F at contact point P2. As illustrated in FIG. 3E, once tissue fold F is stretched across distal tip 24 of flexible tube 14, sharpened needle or obturator 34 may be extended from distal tip 24 of flexible tube 14 to pierce all four layers of the tissue wall W. Sharpened needle or obturator 34 is inserted via inlet 35 to flexible tube 14 on handle 16 (see FIG. 1A).

As discussed above, the GI lumen comprises an inner mucosal layer, connective tissue, the muscularis layer and the serosa layer. To obtain a durable purchase, e.g., in performing a stomach reduction procedure, the staples or anchors used to achieve reduction of the GI lumen preferably engage at least the muscularis tissue layer, and more preferably, the serosa layer as well. Advantageously, stretching of tissue fold F across distal tip 24 permits an anchor or length of suture to be ejected through both the muscularis and serosa layers, thus enabling durable gastrointestinal tissue approximation.

As depicted in FIG. 3E, after tissue fold F is stretched across distal tip 24 of flexible tube 14 to form contact point P2 with tissue wall W, needle 34 may be extended from distal tip 24 and through tissue fold F. Because needle 34 penetrates the tissue wall twice, it exits within the GI lumen, thus reducing the potential for injury to surrounding organs. Once the needle has penetrated tissue fold F, an anchor assembly or length of suture may be ejected through distal tip 24. The deployment of anchors through needle 34 as well as other variations of the apparatus 10 may be seen in further detail in U.S. patent application Ser. No. 10/735,030 which has been incorporated herein by reference above.

The apparatus 10, as described above, may be further utilized in suturing the newly formed tissue fold F in an interrupted, continuous, or running suture depending upon the length of the newly formed tissue fold and the desired method of tissue fold securement. As shown in the detail assembly view of FIG. 4, jaw assembly 36 and jaw members 28a, 28b may be freely rotatable about its longitudinal axis relative to flexible tube 13 and catheter tube 11, as indicated by the arrow C. Moreover, a secondary grasper assembly 37 having a secondary grasper 39 on a distal end of tubular member 38 may be slidably positioned within flexible tube 14. Grasper 39 may be articulated between an open and close configuration from its proximal end preferably located within handle 16.

Grasper 39 may generally comprise a variety of graspers but is preferably configured to grasp and hold onto a needle such as needle body 40. As shown illustratively in FIG. 4, needle body 40 may generally be configured as a needle having one or two tapered piercing ends on opposing sides of needle body 40. A suture attachment point 41, e.g., an eyelet or opening, may be defined along needle body 40 and serve as an attachment point for a length of suture 42.

Figure 4:
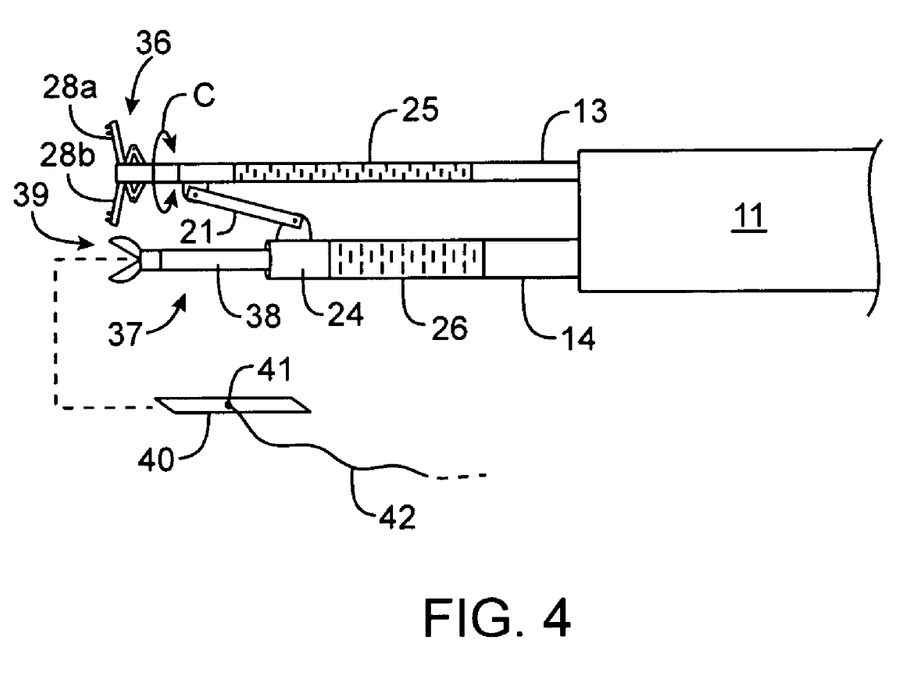
FIG. 4 shows another variation of the endoscopic device having a rotatable tissue grasping assembly which may be used in creating a continuous stitch in tissue.

Grasper 39 and flexible tube 38 may define a passage or lumen through which needle body 40 may be passed. Alternatively, grasper 39 and flexible tube 38 may be configured to retain needle body 40 at least partially therein and grasper 39 may be at least partially retracted within flexible tube 14 by the proximal translation of flexible tube 38. As mentioned above, needle body 40 may be configured in a variety of ways, e.g., a needle body having a piercing tapered end and a balled proximal end to facilitate grasping of the needle body. Other variations of the needle body 40 and grasper 39 may be seen in further detail in U.S. patent application Ser. No. 10/989,684 filed Jul. 23, 2004, which is incorporated herein by reference in its entirety.

Figure 5A:
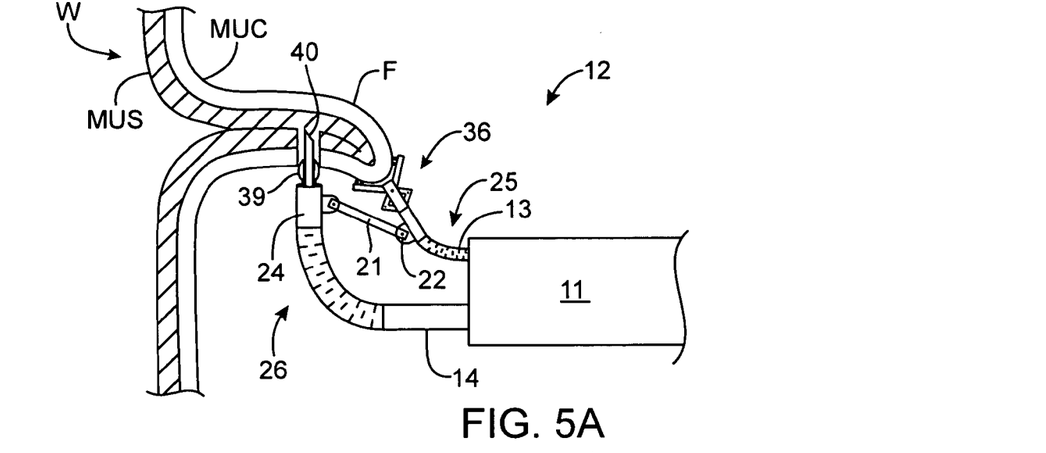
FIGS. 5A to 5F show side views illustrating another example of a method for forming and suturing a tissue fold with a continuous running stitch.

In operation, the tissue wall W may be grasped and approximated and flexible tube 14 may be curved to align distal tip 24 transversely relative to the tissue fold F, as described above. However, in this variation and as shown in FIG. 5A, needle body 40 may be advanced and pierced into and/or through tissue fold F via grasper 39 being advanced distally through flexible tube 14. The tissue wall W is shown in this and the following figures as having at least a mucosa layer MUC and an underlying muscularis layer MUS as typically found in hollow body organs such as the stomach, although the device and methods are not limited to use in only the GI tract of a patient.

Figure 5B:
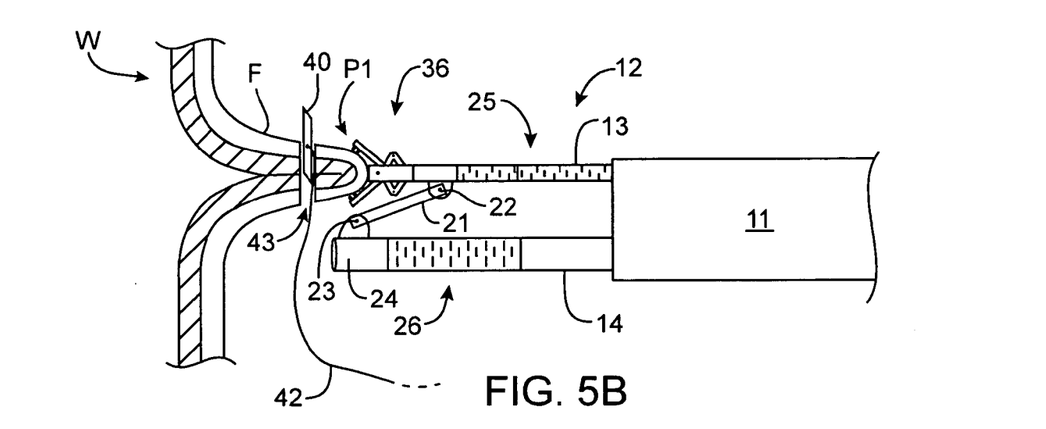

As seen in FIG. 5B, once needle body 40 has been advanced through or at least partially through tissue fold F, needle body 40 may be released by grasper 39 and flexible tube 38 may be retracted from tissue fold F. Suture 42 remains attached to needle body 40 and is routed through the tissue passage 43 created by needle body 40. Suture 42 may be disposed and/or anchored within or proximally of flexible tube 14 or it may simply be ejected therefrom.

Figure 5C:
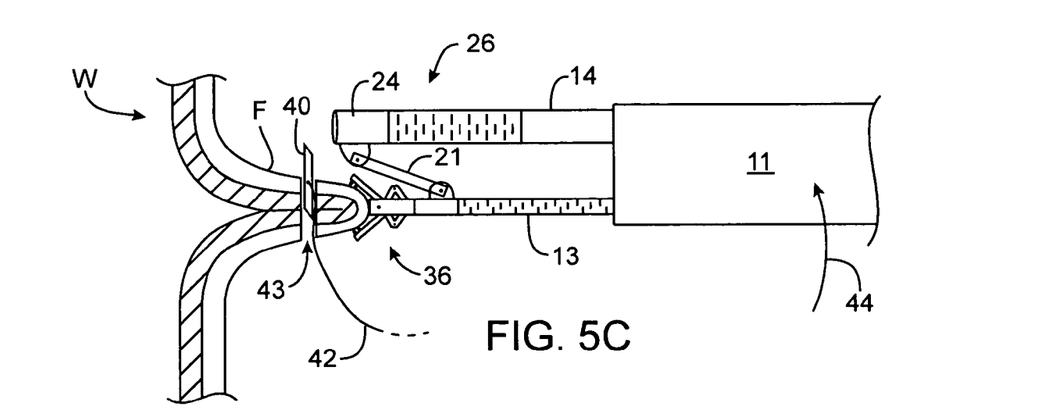

Once grasper 39 has been retracted from tissue fold F, the entire apparatus and catheter body may be rotated relative to tissue fold F such that flexible tube 14 becomes aligned on the opposite side of tissue fold F, i.e., on the side of the tissue where needle body 40 exits tissue fold F, as shown in FIG. 5C. In this example, rotatable grasper 36 may keep its grasp on tissue fold F to maintain a position of catheter 11 relative to tissue fold F and needle body 40 while the device is rotated in the direction as shown by arrow 44.

Figure 5D:
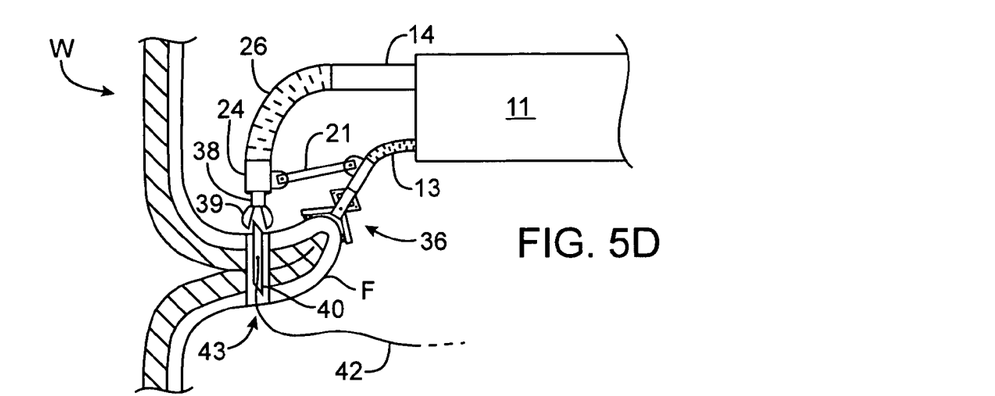
Figure 5E:
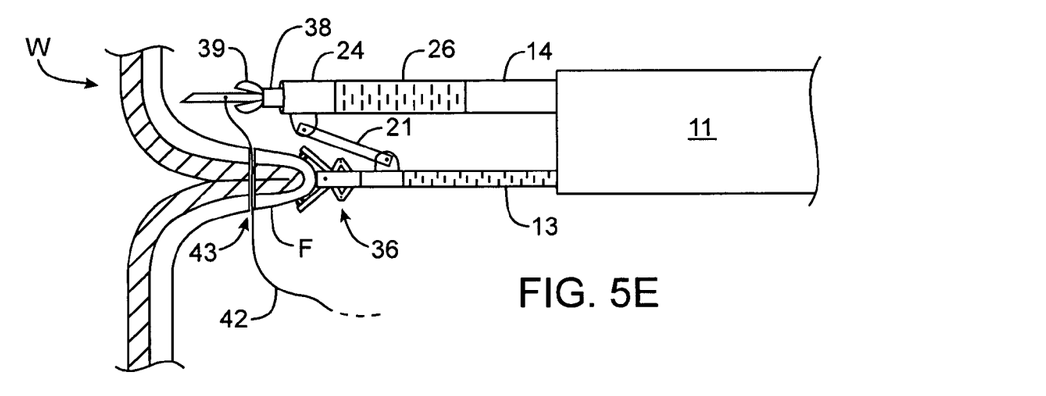

As shown in FIG. 5D, once the device has been realigned, flexible tube 14 may again be manipulated to bend such that distal tip 24 is aligned transversely relative to tissue fold F. Flexible tube 38 may then be advanced distally and grasper 39 may be actuated to receive and grasp onto needle body 40. Once grasper 39 has clamped or grasped onto needle body 40, flexible tube 38 and/or flexible tube 14 may be pulled proximally to remove needle body 40 from tissue fold F, as shown in FIG. 5E. Suture 42 may be seen as passing through tissue fold F and desirably through the overlapped muscularis layers.

Figure 5F:
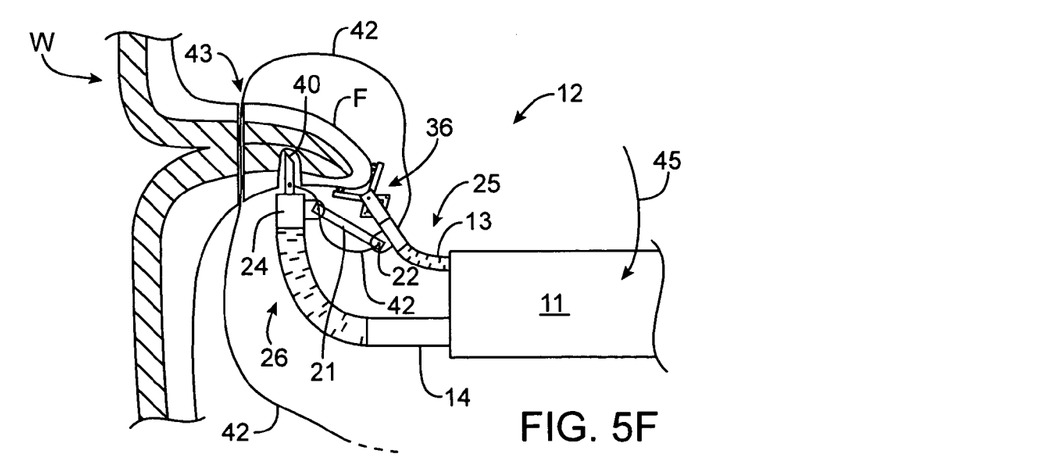

While grasper 39 maintains its hold on needle body 40, the device may again be rotated to realign flexible tube 14 back to the other side of tissue fold F, as shown in FIG. 5F by the direction of rotation of arrow 45. Once flexible tube 14 is desirably positioned, it may again be manipulated distally to align distal tip 24 transversely relative to tissue fold F which may again be pierced by advancing needle body 40 into or through tissue fold F at another location adjacent to the originally formed tissue passage 42. While the device and needle body 40 is rotated and re-rotated relative to the tissue fold F, suture 42 may be looped about tissue fold F any number of times in a continuous or running suture depending upon the desired length of suture 42 and the desired suturing effects.

When rotated, the device may be rotated about rotatable grasper 36 as it maintains its hold onto tissue fold F. Alternatively, rotatable grasper 36 may release the tissue and the entire device may be relocated along the tissue wall W to another position.

To facilitate the endoscopic suturing of the tissue within the hollow body organ, the area of interest may be visualized through a number of methods. For instance, a laparoscopic camera may be introduced into the area percutaneously to provide a visual image. Alternatively, visualization of the tissue area of interest and of the tissue fold formation and suturing procedure may be visualized endoscopically by positioning an imager, e.g., CCD camera, optical fibers, etc., into the distal end of catheter 11.

Figure 6A:
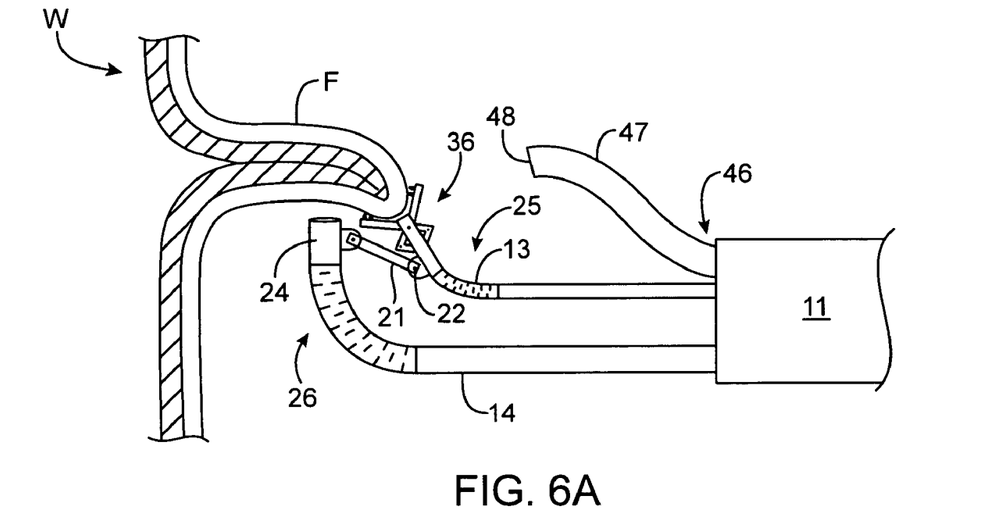
FIGS. 6A and 6B show side views of an endoscopic device with alternative variations for endoscopically visualizing a tissue folding and/or suturing procedure.

Alternatively, as shown in FIG. 6A, an endoscope having a sufficiently small-sized diameter, e.g., a gastroscope 47, may be introduced into the area by advancing the gastroscope 47 through a scope lumen 46 defined through torqueable catheter 11. Gastroscope 47 may be advanced such that its distal end extends no farther than the distal end of catheter 11 to provide images via an imager 48, e.g., CCD camera, optical fibers, etc. In another example, the gastroscope 47 may be advanced beyond catheter 11 and proximally adjacent of tissue fold F. In such a case, gastroscope 47 is preferably configured to, have a manipulatable distal end portion such that articulation of the distal portion of the gastroscope 47 into at least a partially retroflexed configuration is achievable. Having an off-axis imager 48 relative to tissue fold F and catheter 11 may provide for triangulation of the image and an improved image of the tissue area.

Figure 6B:
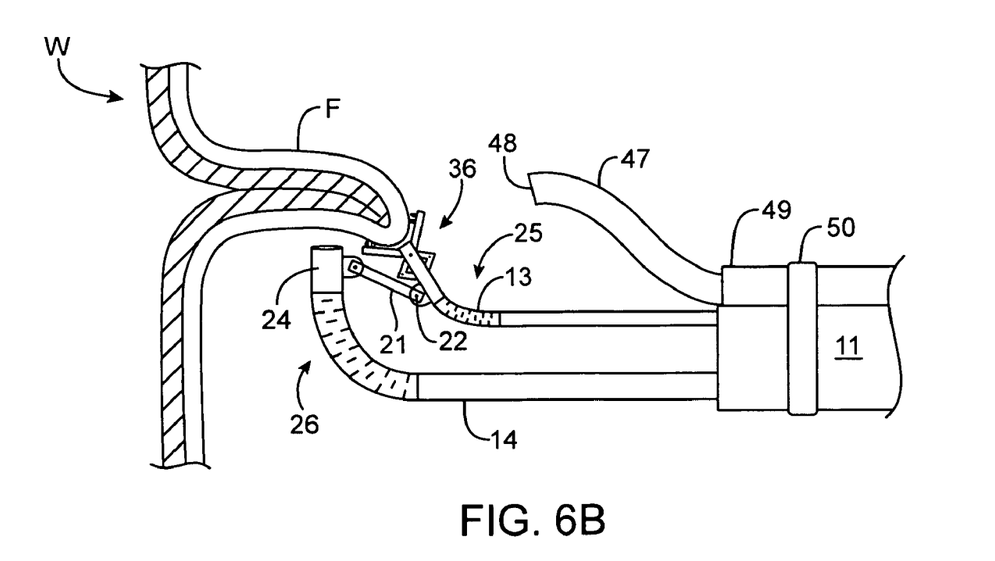

FIG. 6B shows an alternative configuration where rather than passing gastroscope 47 within a scope lumen defined through catheter 11, an external scope lumen 49 may be attached along an outer surface of catheter 11 through a variety of methods, e.g., via a plurality of bands 50. Gastroscope 47 may then be advanced through external lumen 49 towards tissue fold F for imaging.

Figure 7:
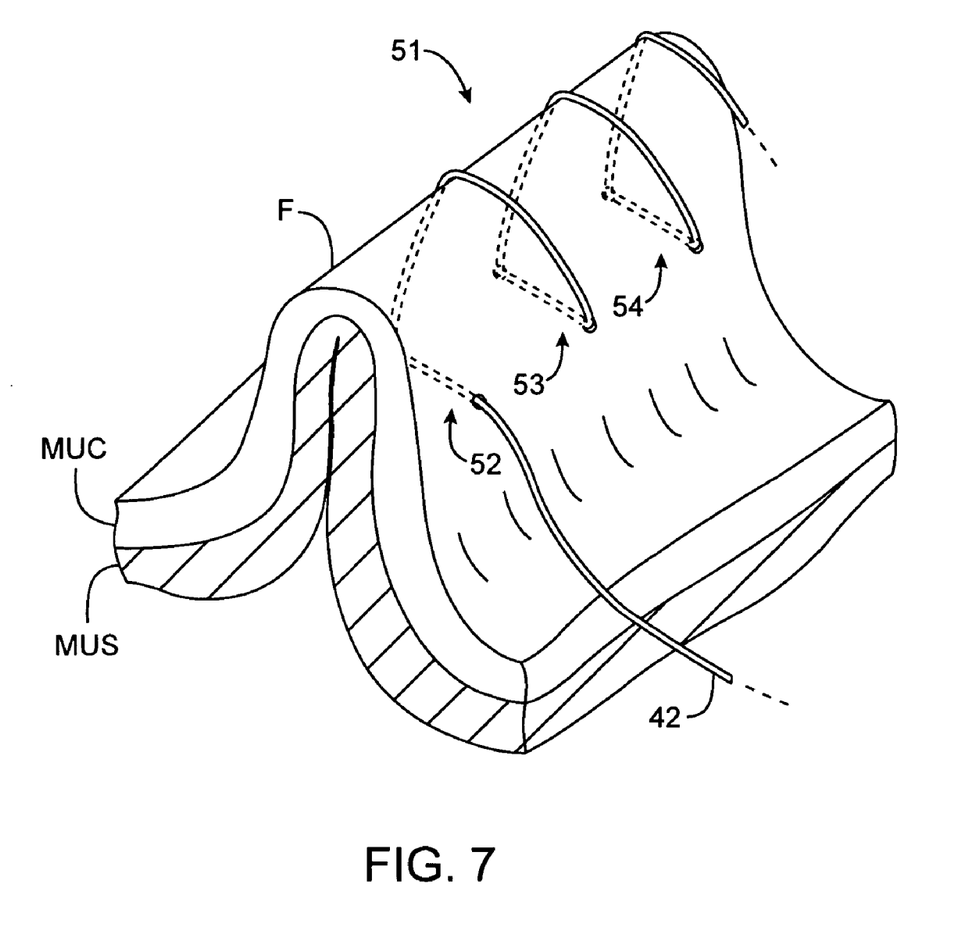
FIG. 7 shows a perspective partial view of a resulting tissue fold which was secured via a continuous running stitch.

As mentioned above, multiple suture loops may be achieved using the devices and methods above depending upon the desired suturing configurations. FIG. 7 shows a partial perspective view of a tissue ridge which may be secured by a continuous running suture loop 51 formed entirely endoscopically. In this particular configuration, suture 42 may be passed through multiple adjacent tissue securement passages 52, 53, 54 with a continuous length of suture 42. Other endoscopic suturing configurations are possible and the figure is intended merely to be illustrative of one type of the running sutures which are achievable. The other suturing configurations depend merely upon the desired suturing effects and are not limited by the illustrations shown herein.

Figure 8A:
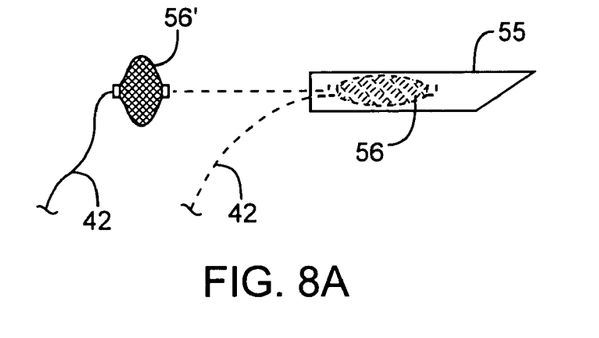
FIG. 8A shows a side view of a deployable anchor which may be positioned within a needle body for deployment against a tissue fold.

In yet another alternative, the needle body may be configured to carry a tissue anchor within a lumen or channel within the needle body. One example is shown in FIG. 8A, which shows another variation of needle body 55 having a channel defined therein sufficiently sized to retain expandable tissue anchor 56. Anchor 56 may have suture 42 attached thereto and trailing proximally out from needle body 55.

Anchor 56 may comprise any number of various tissue anchors preferably designed for placement against a soft tissue surface. For instance, anchor 56 may comprise an expandable anchor made of a meshed material which allows for reconfiguration between a low-profile delivery configuration, as seen within needle body 55, and an expanded deployment configuration, as seen in anchor 56' when unconstrained by needle body 55. The reconfiguration of the anchor may be effected by a self-expanding metallic alloy material, such as Nitinol, or it may be effected by a meshed polymeric material which configures into an expanded shape against a tissue surface when suture 42 is tensioned. Other examples of various types of tissue anchors which may be utilized are described in further detail in U.S. patent application Ser. No. 10/869,472 filed Jun. 15, 2004 and U.S. patent application Ser. No. 10/612,170 filed Jul. 1, 2003, both of which are incorporated herein by reference in their entirety.

Figure 8B:
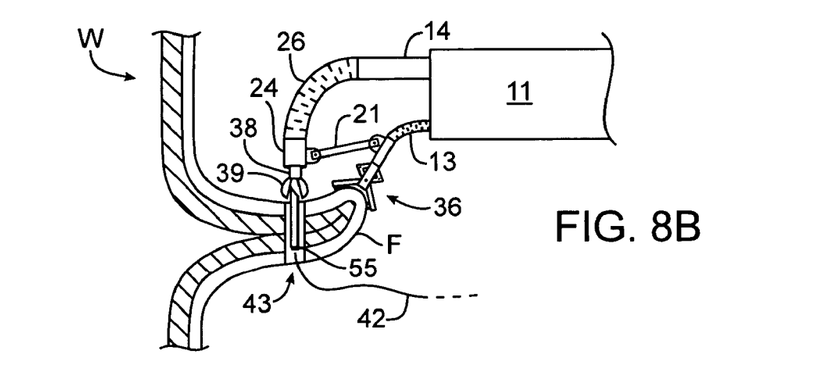
FIGS. 8B and 8C show one example of how an expandable anchor may be deployed from a needle body passed through a tissue fold.
Figure 8C:
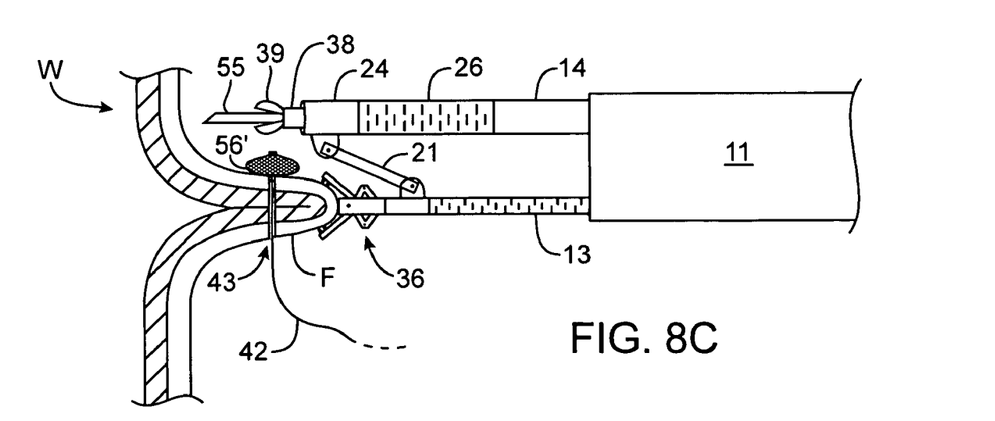

An example of how such a deployable anchor may be utilized may be seen in FIGS. 8B and 8C. The needle body 55 may be deployed through tissue fold F in the same or similar manner as described above by forming tissue fold F and passing needle body 55 partially into or through the tissue. As seen in FIG. 8B, with anchor 56 positioned within needle body 55 and suture 42 trailing therefrom, needle body 55 may be grasped by grasping assembly 39 and pulled through the tissue. Once free, anchor 56 may be ejected from needle body 55, e.g., by pulling suture 42 or actively urging anchor 56 from needle body 55 via an elongate pusher or catheter. Anchor 56' may then be unconstrained to expand into a deployment configuration and subsequently pulled tight against tissue fold F by tensioning suture 42. Once tensioned, suture 42 may be utilized to secure tissue fold F or to hang other objects therefrom.

Although a number of illustrative variations are described above, it will be apparent to those skilled in the art that various changes and modifications may be made thereto without departing from the scope of the invention. Any of the modifications to endoscopic suturing apparatus and methods may be done in a variety of combinations with one another, as practicable. Any of the combinations or modifications is intended to be within the scope of this invention. It is further intended in the appended claims to cover all such changes and modifications that fall within the true spirit and scope of the invention.

What is claimed is:

1. A method for endoscopically suturing a region of tissue, comprising:

endoscopically advancing an elongate tubular member to the region of tissue;

engaging the region of tissue with a tissue engagement device comprising a pair of jaws and a flexible tube extending from a distal end of the elongate tubular member;

approximating the tissue relative to the elongate tubular member via the tissue engagement device;

using the approximating motion to simultaneously curve a distal end of a deployment tubular member extending from the elongate tubular member via a linkage pivotably connecting the tissue engagement device and the deployment tubular member such that a distal tip of the deployment tubular member is aligned substantially transversely with the tissue;

deploying a needle body and a length of suture depending therefrom at least partially into or through the tissue from the deployment tubular member;

rotating the deployment tubular member and the flexible tube about a longitudinal axis of the pair of jaws while the tissue engaging device is engaging the region of tissue; and grasping the deployed needle body with a needle grasper slidably positioned within the deployment tubular member.

2. The method of claim 1 wherein endoscopically advancing an elongate tubular member comprises advancing the tubular member transesophageally into a stomach.

3. The method of claim 1 wherein engaging the region of tissue comprises temporarily engaging the region of tissue.

4. The method of claim 1 wherein approximating the tissue comprises pulling the tissue proximally into a fold via the tissue engagement device.

5. The method of claim 1 wherein deploying a needle body comprises urging the needle body into the tissue via the needle grasper.

6. The method of claim 1 wherein grasping the deployed needle body comprises drawing the needle body into deployment tubular member via the needle grasper.

7. The method of claim 1 further comprising rotating the deployment tubular member about the longitudinal axis while holding the needle body.

8. The method of claim 7 further comprising deploying the needle body and the length of suture through the tissue such that the tissue is secure.

9. The method of claim 1 further comprising deploying an expandable anchor from the needle body for placement against the tissue.

* * * * *